(12) United States Patent
Ziemer

(10) Patent No.: US 6,623,498 B1
(45) Date of Patent: Sep. 23, 2003

(54) CUTTING INSTRUMENT

(75) Inventor: Frank Ziemer, Port (CH)

(73) Assignee: SIS Ltd., Biel-Bienne (CH)

( * ) Notice: Subject to any disclaimer, the term of this patent is extended or adjusted under 35 U.S.C. 154(b) by 0 days.

(21) Appl. No.: 09/715,016

(22) Filed: Nov. 20, 2000

Related U.S. Application Data (62) Division of application No. 09/247,528, filed on Feb. 10, 1999, now Pat. No. 6,165,189.

(51) Int. Cl.$^7$ .................................................. A61F 9/00
(52) U.S. Cl. ....................................................... 606/166
(58) Field of Search ........................... 606/1, 166, 167, 606/170, 171, 169, 172, 180; 30/43.7, 42

(56) References Cited

U.S. PATENT DOCUMENTS

| | | | |
|---|---|---|---|
| 4,508,121 A | | 4/1985 | Myers |
| 4,526,171 A | * | 7/1985 | Schachar .................... 606/166 |
| 4,662,370 A | | 5/1987 | Hoffmann et al. |
| 5,133,726 A | | 7/1992 | Ruiz et al. |
| 5,288,292 A | * | 2/1994 | Giraud et al. ................. 33/512 |
| 5,690,657 A | | 11/1997 | Koepnick |
| 5,989,272 A | * | 11/1999 | Barron et al. ............... 606/161 |
| 5,997,559 A | * | 12/1999 | Ziemer ....................... 606/166 |
| 6,007,553 A | * | 12/1999 | Hellenkamp et al. ....... 606/166 |
| 6,022,365 A | * | 2/2000 | Aufaure et al. ............. 606/166 |
| 6,045,562 A | * | 4/2000 | Amano et al. .............. 606/166 |
| 6,059,805 A | * | 5/2000 | Sugimura et al. ........... 606/166 |
| 6,203,555 B1 | * | 3/2001 | Amano et al. .............. 606/166 |
| 6,302,896 B1 | * | 10/2001 | Carriazo et al. ............ 606/166 |

FOREIGN PATENT DOCUMENTS

| | | |
|---|---|---|
| JP | 61-73657 A | 4/1986 |
| JP | 10-183 A | 1/1998 |
| JP | 11-019115 A | 1/1999 |
| JP | 11342151 A | 12/1999 |
| WO | WO 98/27901 A1 | 7/1998 |
| WO | WO 98/48747 A2 | 11/1998 |
| WO | WO 98/53774 A1 | 12/1998 |

OTHER PUBLICATIONS

U.S. patent application Ser. No. 09/129,365, Ziemer, filed Aug. 5, 1998.

* cited by examiner

*Primary Examiner*—Kevin T. Truong
*Assistant Examiner*—Victor Nguyen
(74) *Attorney, Agent, or Firm*—Rothwell, Figg, Ernst & Manbeck (57) ABSTRACT

The microkeratome comprises a holder (1) with a suction ring (11) for attachment to the sclera of a patient's eye and having means (23) for connection to a suction source. A slide (2) is displaceably mounted on the holder (1) in a linear guide thereof. The slide (2) has a plane contact surface for contacting the cornea of the patient's eye and slideable over the cornea in a direction parallel to the contact surface. The slide contains a cutting blade with a cutting edge which is parallel to the contact surface. A first motor moves the slide on the holder. The blade is mounted in the slide for oscillating movement in a direction parallel to the cutting edge. A second motor oscillates the blade. The two motors are mounted on a common motor unit which is detachably mounted to the slide. The holder has a grip portion surrounding the motor unit on two lateral sides and a rear side.

10 Claims, 11 Drawing Sheets

| STEP/STATUS | LEFT FOOT SWITCH | RIGHT FOOT SWITCH |
|---|---|---|
| READY TO SWITCH ON VACUUM | ABORT | VACUUM ON |
| VACUUM ON | VACUUM OFF | READY |
| DRIVE TO INITIAL POSITION | STOP | STOP |
| CONFIRM PARAMETERS AND ADHERENCE TO EYE | ABORT | CONFIRM |
| START CUT | ABORT | START CUT |
| CUT IS STARTED | STOP | STOP |
| CUT IS STOPPED (EXCEPTION) | ABORT | RESTART |
| CUT FINISHED, VACUUM ON | | VACUUM OFF |
| CUT FINISHED, VACUUM OFF | END | VACUUM ON |

CUTTING INSTRUMENT

CROSS-REFERENCE TO RELATED APPLICATIONS

The present application is a divisional of U.S. application Ser. No. 09/247,528, to Frank Ziemer, filed Feb. 10, 1999, now U.S. Pat. No. 6,165,189.

FIELD OF THE INVENTION

The present invention concerns a microkeratome for performing LASIK surgery.

BACKGROUND OF THE INVENTION

LASIK (Laser Assisted In-Situ Keratomileusis) is a procedure commonly used to treat Myopia (nearsightedness), Hyperopia (farsightedness), and Astigmatism through the use of the Excimer Laser. LASIK is an operation which is performed in the Excimer Laser suite. The whole procedure is done under topical anesthesia (numbing drops) and its entire duration is seldom longer than 10 minutes. A suction ring of about 20 mm diameter is placed over the sclera (the white part of the eye) to hold the eye firmly. In performing LASIK, the surgeon first uses a microkeratome, presently with a special oscillating steel blade, to make a partial cut through the front surface of the cornea. This creates a flap of clear tissue on the front central part of the eye. So the automated microkeratome passes across the cornea to create a thin flap This part of the operation usually takes only a few seconds. The suction ring is then retired from the eye, and the flap is lifted back to leave enough room for the usage of the Laser. The Excimer Laser, which has been previously programmed specifically for the correction of the desired amount of the visual effect, is then applied. A rapid, continuous emission of Laser pulses removes very small, precise amounts of corneal tissue. Depending on the type of refractive error, this part of the surgery takes between 30 to 60 seconds. The cornea is then irrigated with saline solution, and the flap is folded back to its original position. Within minutes, the flap adheres itself to rest of the cornea and the LASIK procedure is done. In a couple of days, the cornea will be crystal clear and almost an imperceptible scar will barely be seen.

U.S. Pat. No. 5,133,726 describes a microkeratome. It comprises a holder with a suction ring for attachment to the sclera of a patient's eye. A suction source is connected to the suction ring. A slide is displaceably mounted on the holder in a linear guide. The slide has a plane frontal surface including a transparent plate for contacting the cornea of the patient's eye and slideable over the cornea in a direction parallel to the frontal surface. Attached to the slide is a flexible shaft which is driven by the motor. The end of the shaft has a threaded area which engages a pinion. The pinion drives via transmission gears a drive gear that engages in a rack on the holder to move the slide. At the extreme end of the shaft an eccentric is formed which engages a slot in a sled displaceably mounted on the slide. On the sled a steel cutting blade is mounted with a cutting edge which is parallel to the frontal surface. In operation, when the motor is started it simultaneously oscillates the blade parallel to the cutting edge and moves the slide on the holder. With this microkeratome the surgeon needs a lot of practice to position and to fix the abutting surface provided to stop the motor at the right time, i.e. at the right place. The abutting surface is to guarantee that the desired width of the remaining hinge linking the cut flap of tissue with the remaining cornea is obtained. The speed and oscillation frequency are fixed and have a fixed ratio determined by the gearing.

SUMMARY OF THE INVENTION

The problem to be solved with the present invention is to provide an improved microkeratome. This problem is solved by the combination of features disclosed hereinafter.

BRIEF DESCRIPTION OF THE DRAWINGS

A preferred embodiment of the invention is hereinafter described with reference to the drawings, in which FIG. 13 is a cross section along the top surface of part of the holder, and.

DETAILED DESCRIPTION OF THE PREFERRED EMBODIMENTS

Figure 10:
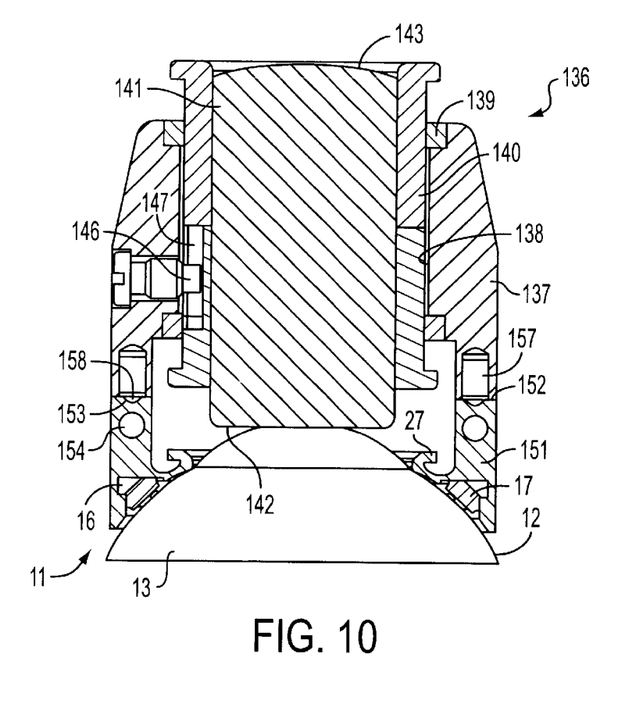

The microkeratome comprises a holder 1 with a suction ring 11 for attachment to the sclera 12 of a patient's eye 13 (see FIG. 10). The suction ring 11 has two spherical surfaces 14, 15 (FIG. 5) and an annular recess 16 between them. A circular ring-shaped insert 17 is detachably mounted in the recess 16 (see FIG. 5 and 10). The insert 17 has radially extending notches 18 with contact surfaces 19 which are rounded on all sides for contacting the eye and which lay in the same sphere as the surfaces 14, 15. Between adjacent notches 18 the insert 17 has through holes 20 which communicate with the recess 16 behind the insert 17. This recess 16 is connected to a channel 22 which at the rear end of the holder communicates with a connector 23 for connecting to a suction pump.

Figure 2:
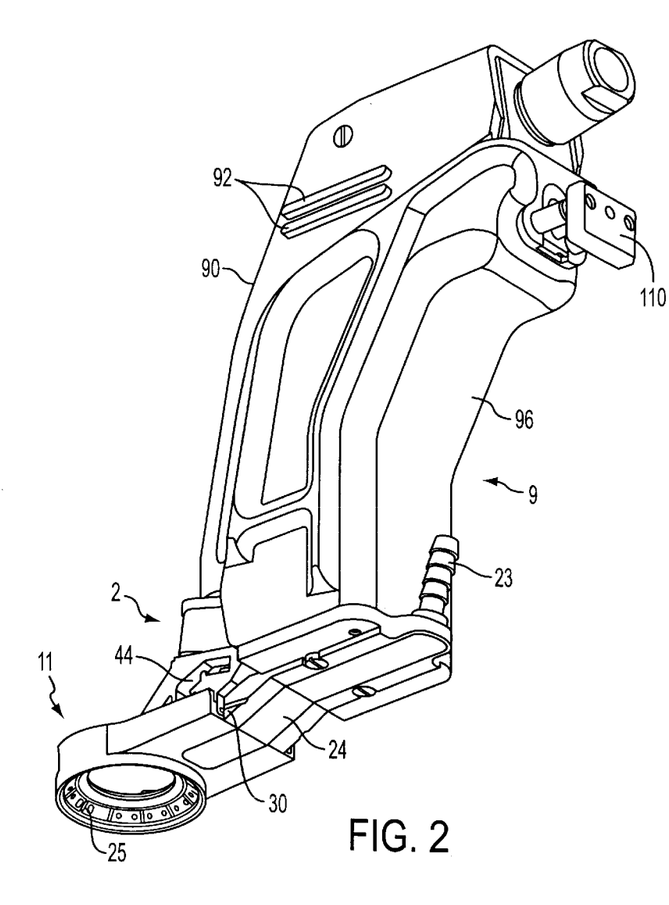
Figure 5:
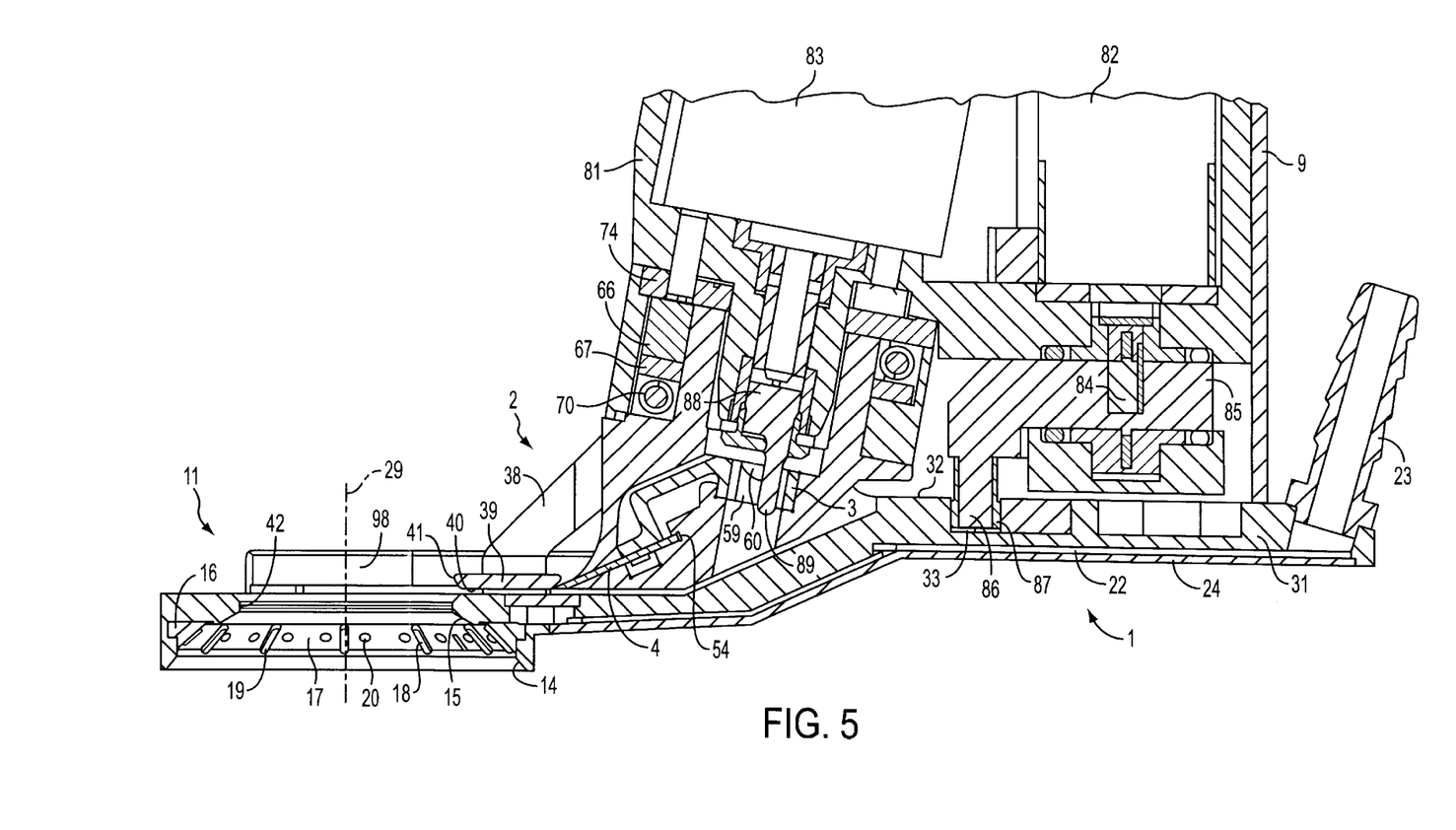

A cover plate 24 extends along and covers the channel 22 (see FIG. 2 and 5). The removable insert 17 has the advantage that the recess 16 and insert 17 can easily be cleaned and sterilized after use. The insert 17 is of metal and slotted on one spot of its circumference so that it can easily be removed by tweezers (see slot 25 in FIG. 2).

Figure 6:
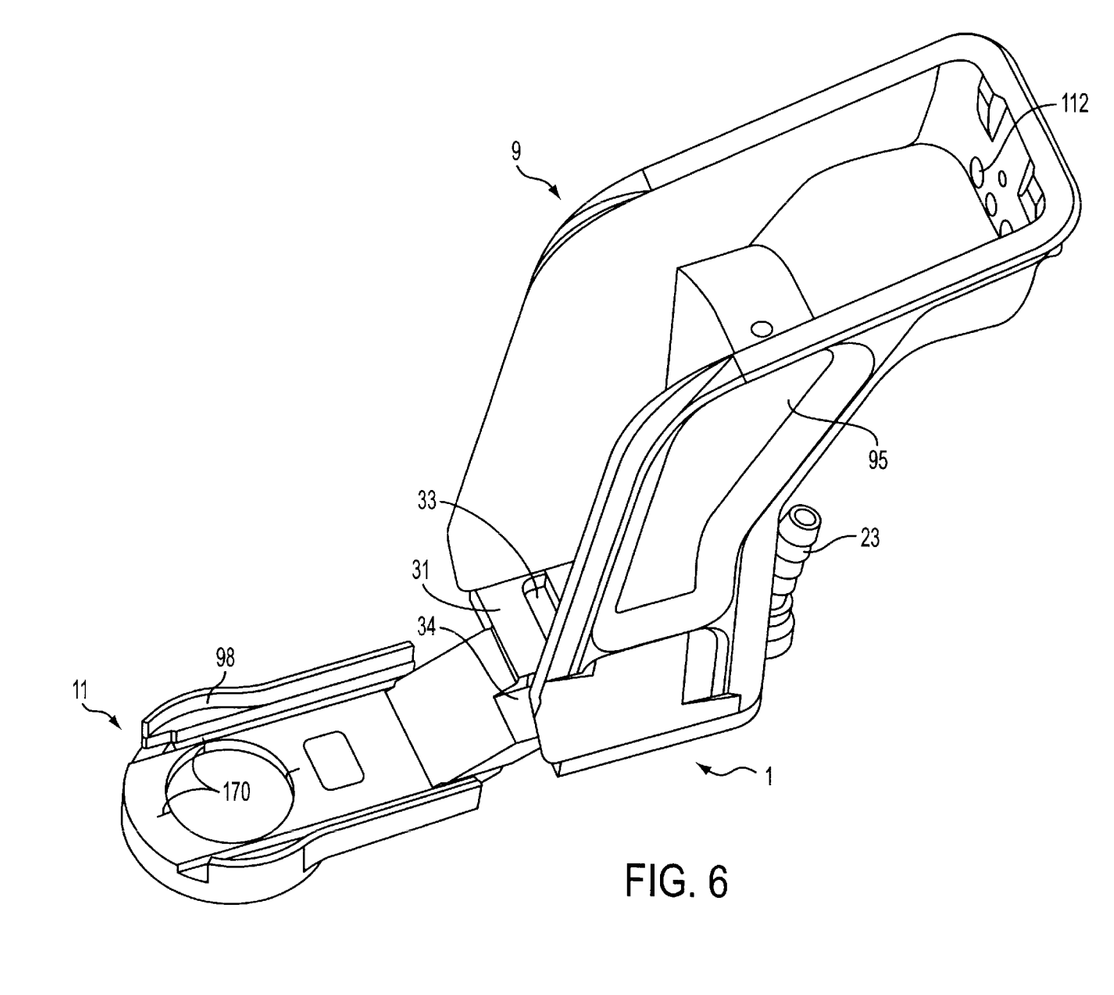
FIGS. 6 is a perspective view of the holder with grip unit.
Figure 13:
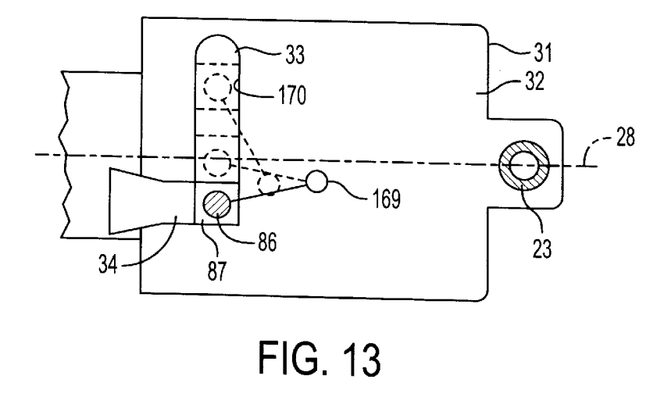

The holder 1 has two rectilinear directing guide rails 27 (FIG. 10) which are symmetrical to the longitudinal middle plane 28 (FIG. 13) extending through the axis 29 of the ring 11. The rails 27 face away from the middle plane 28. The longitudinal extension of the rails 27 is perpendicular to the axis 29. This particular and uncommon arrangement of the rails 27 has the advantage that the moving slide 2 described below which has guide grooves 30 guided in the rails 27, on the line where the moving slide 2 meets the holder 1, does not contact and jam or squeeze the tissue of the eye. Thereby, injuries of the eye and pressure changes during cutting can be avoided. A rear, raised part 31 of the holder has an upper surface 32 which is perpendicular to the axis 29. The part 31 has a rectilinear groove 33 extending perpendicular to and across the middle plane 28. On one end the groove 33 merges into a longitudinally extending groove 34 which is open towards the forward end (FIG. 6 and 13).

Figure 7A:
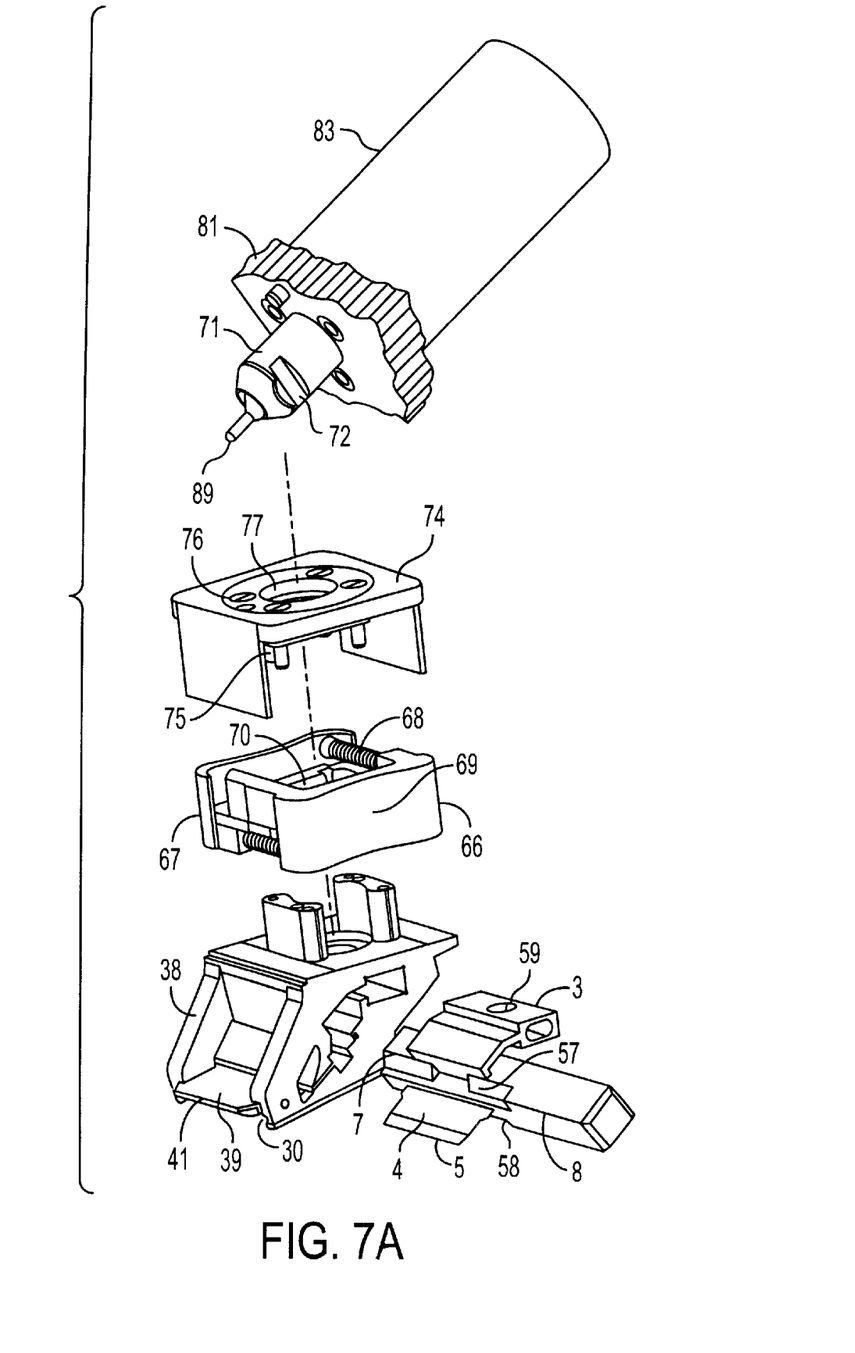
FIGS. 7a–7b are a perspective view of the parts of the slide.
Figure 7B:
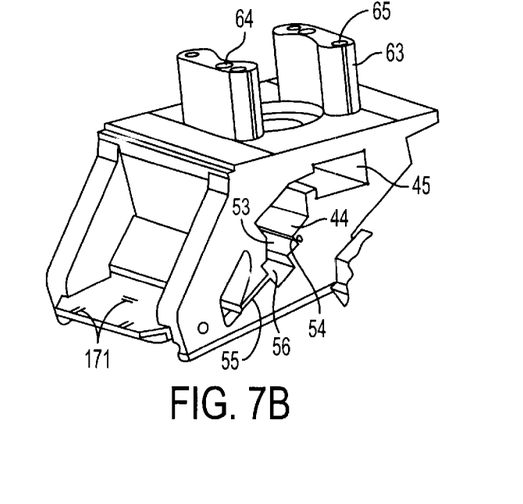
Figure 8A:
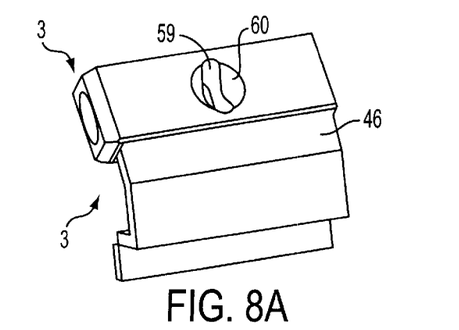
FIGS. 8a to 8c show the parts of the sled.
Figure 8B:
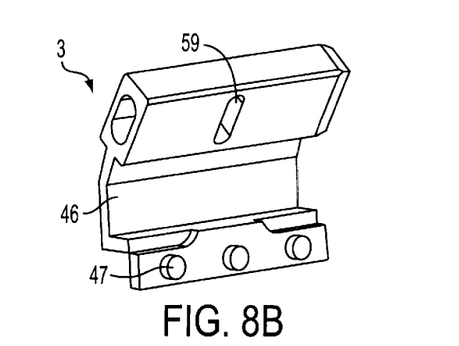

The guide grooves 30 of the slide 2 are best seen in FIG. 7a which shows the parts of the slide 2, a sled 3 (FIG. 7, 8a and 8b) with a cutting blade 4 having a cutting edge 5, part of a motor unit 6 removeably mounted on the slide 2, a mounting help 7 and a handle 8 for the sled 3. The slide 2 has two lateral arms 38 on which a transverse plate 39 is mounted with a plane contact surface 40 for contacting the cornea of the eye 13. The surface 40 is perpendicular to the axis 29 and therefore parallel to the guide rails 27 and grooves 30. In a park position shown in FIG. 5 the forward end face 41 of the plate 39 is slightly behind the opening 42 of the ring 11. This allows free access to the eye in the park position, e.g. for purposes described later. The plate 39 may be transparent, e.g. of glass, and may have marks for reading the diameter of the contact area of the plate 39 with the eye 13 for the purposes more specifically described in U.S. patent application Ser. No. 09/129,365 by Frank Ziemer, filed Aug. 5,1998, and incorporated herein by reference.

Figure 1:
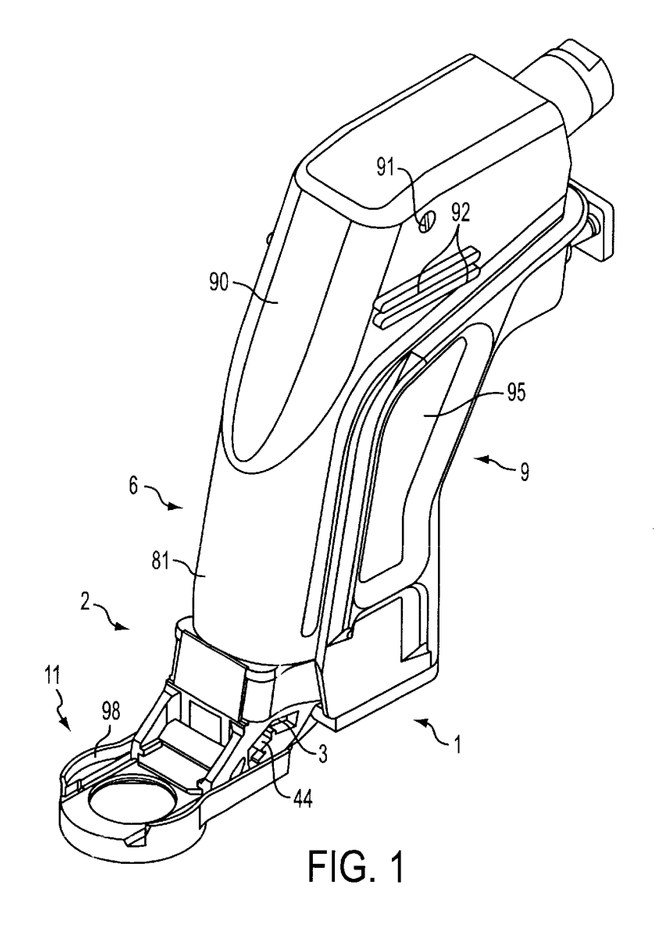
FIGS. 1 and 2 show perspective views of the microkeratome.
Figure 8C:
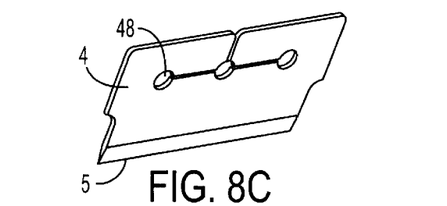

The slide 2 has a transverse, prismatic opening 44 (FIG. 1 and 7b) in which the prismatic, thermoplastic sled 3 is guided. The opening 44 extends perpendicular to the axis 29 and the rails 27 and is open to both sides. In a part 45 of the opening 44 with rectangular cross section the sled 3 is guided. An elastic arm 46 integrally formed on the sled 3 has attachment pins 47 formed on it. The blade 4 (FIG. 8c) has corresponding holes 48 which match the pins 47. The blade 4 is attached to the sled 3 by thermoplastic deformation of the free ends of the pins 47.

The arm 46 elastically biases the blade 4 against the first guide surface 53 and the second guide surface 54 (FIG. 7b) which are perpendicular to each other and are part of the opening 44. The surface 53 is coplanar with a lower surface of a slot 55 through which the blade 4 extends. The cutting edge 5 extends to about 0,16 mm below the plane of the contact surfaces 40. Preloading the blade 4 by the arm 46 has the advantage that the play of the sled 3 in the opening 44 and of the blade 4 in the slot 55 does not have any influence on the accurate guidance of the blade 4 in operation. Therefore, the spacing between the cutting edge 5 and the plane of the surface 40 remains accurate to within a few $\mu$m.

The prismatic mounting help 7 and the handle 8 each have the same cross section as a forward part 56 of the opening 44. They each have prismatic or cylindrical extensions 57 which formlockingly engage the sled 3 and/or the arm 46. The mounting help 7 is tapered at the forward end to facilitate introduction into part 56 of openings 44. The handle 8 has, spaced from the sled 3; a step 58. The sled 3 has a transverse slot 59 extending perpendicular he opening 44. A conical counters sink 60 extends from the upper surface of the sled 3 with its axis coinciding with the cent I axis of the slot 59.:

The slide 2 further comprises two prismatic extensions 63 which have centering holes 64 and threaded holes 65 in their end surfaces. Two counteracting ring-shaped locking elements 66, 67 surround the extensions 63 and are spread apart by two springs 68. On a wall opposite a gripping surface 69 each element has a locking bar 70 which in the mounted position of the motor unit 6 engage grooves 72 on a cylindrical extension 71 of the motor unit 6. The elements 66, 67 are held on the slide 2 by a cover unit which is centered with pins 75 in the holes 64 and screwed onto the extensions 63 by screws 76. The unit 74 has a central cylindrical opening 77 in which the extension 71 is centered.

The motor unit 6 (FIG. 1, 3, 5) comprises a casing 81 on which a first motor 82 and a second motor 83 are mounted. The axis of the motor 82 is perpendicular to the rails 27 and the contact surface 40. Its output shaft 84 drives a disc 85 which carries an eccentric in 86. The pin 86 carries a shoe 87 which is square in plan view and engages in the grooves 33, 34. The axis of the motor is inclined rearwardly to gain better access and view to the suction ring 11. The output shaft 88 of the motor 83 has a further eccentric pin 89 which engages in the slot 59 and thereby drives the sled 3. The motor unit 6 is covered by a cover 90 which is fixed to the unit 6 by screws 91 and has on both sides two guide rails 92 for suspension in a stand (not shown).

The grip unit 9 shown in FIG. 2 and 6 consists of metal. The unit 9 has two opposed lateral side walls 95 and a rear wall 96, the lower end of the walls 95, 96 are welded or braced to the top surface 32 of the raised part 31 of the holder 1. The grip unit 9 surrounds the motor unit 6 on at least part of its lateral sides and on its rear side. The surgeon holds the microkeratome on this grip unit during the operation. This grip unit 9, via the holder 1, is fixed with respect to the suction ring 11, while the motor unit 6, together with the slide 2, moves towards the suction ring 11. The larger parts of the microkeratome, in particular the holder 1, the grip unit 9 and the casing 81 are manufactured of titanium to save weight.

As shown particularly in FIG. 6 the holder 1 has along the sides of the periphery of the suction ring 11 and along the rear part of the guide rails 27 an upstanding narrow rim 98. The rim 98 guards the slide 2 from coming into contact with the eye lid. Therefore, the surgeon always has one hand free during the operation.

Figure 3:
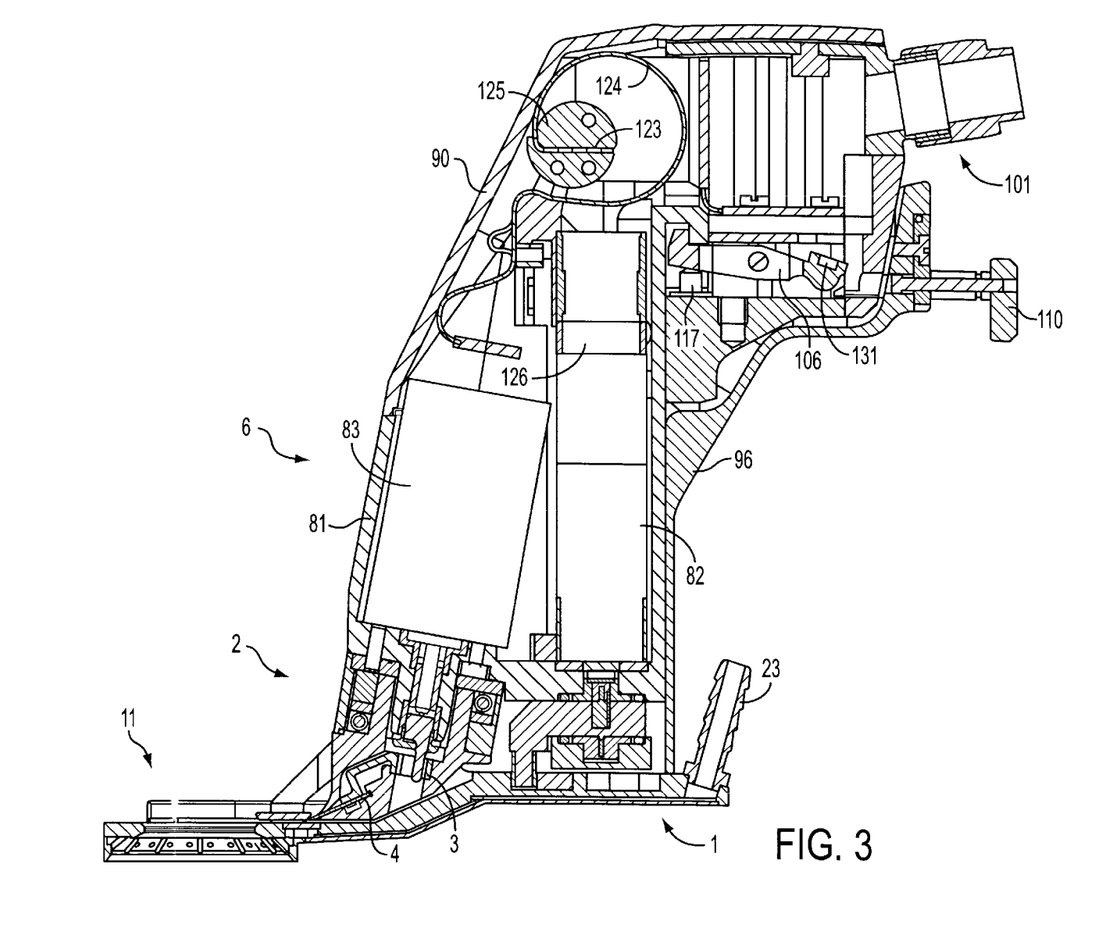
FIGS. 3 to 5 show longitudinal sections.
Figure 4:
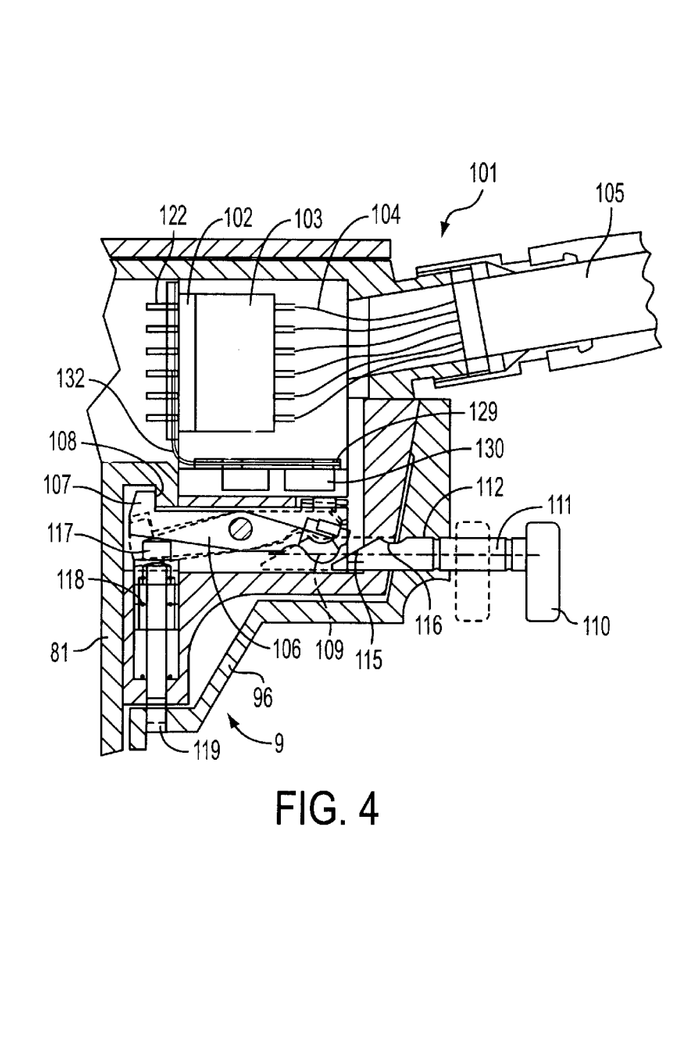

FIG. 4 and the upper part of FIG. 3 further show a cable holder 101 which can be docked alternatively either to the motor unit 6 or to the grip unit 9. In the holder 101 a plug socket 102 is fixed into which a plug 103 is inserted. A plurality of leads 104 of a cable 105 connecting the holder 101 with a control unit are connected to the plug 103. A two-armed lever 106 is pivotably supported in the holder 101. The forward arm of the lever 106 has a hook 107 which in the position shown in FIG. 3 engages a shoulder 108 of the casing 81 of the motor unit 6 and therewith docks the holder to the unit 6. The rear end of the other arm of the lever 106 has a cylindrical extension 109. A pusher 110 is mounted on the upper part of the rear wall 96 of the grip unit 9. The pusher 110 is attached to two cylindrical pins 111 which are slideable in corresponding through-borings 112 of the wall 96. The pins 111 have at the forward end a wedge surface 115 which merges into a cylindrical recess 116.

The lever 106 is urged into its position shown in FIG. 3 by two laterally spaced pins 117 which are pre loaded upwardly by springs 118. FIG. 4 shows a cross section parallel to the longitudinal section of FIG. 3 but containing the axis of one of the pins 117.

When the holder 1 is inserted onto the slide 2 to the position shown in FIG. 3, the pusher 110 is pushed in. The wedge surface 115 pushes the extension 109 upwardly so that the lever 106 pivots counterclockwise against the force of the springs 118. In the fully pushed in position the extension 109 rests in the recess 116 of the pins 111 (shown in dashed lines in FIG. 4). The lower ends of the two pins 117 in that position engage in corresponding borings 119 of the rear wall 96. The hook 107 is out of engagement with the shoulder 108 and the holder 101 is now coupled to the grip unit 9 and therewith to the holder 1. This has the advantage that the cable 105 does not move when the slide 2 with the motor unit 6 moves forward. During cutting the cable does not transmit any forces to the moving unit.

Part of the pins 122 of the socket 102 are connected (not shown) to one end 123 of a band-shaped, flexible electrical cable 124. The end 123 is clamped in a cylindrical drum 125 which is fixed to the connection holder 101. In the park position shown in FIG. 3, the cable 124 surrounds the drum 125 in a loose loop. Its other end is fixed to the motor unit 6 and its various leads are connected to the motors 82, 83 and to an angle sensor 126 which is coupled to the output shaft 84 of the motor 82 as a feedback of the position of the slide 2 on the holder 1.

An electronic circuit plate 129 comprising a hall sensor 130 is mounted on the holder 101 above the lever 106. The extension 109 contains a permanent magnet 131 cooperating with the hall sensor 130. The plate 129 is connected by leads 132 to some of the pins 122.

Figure 9:
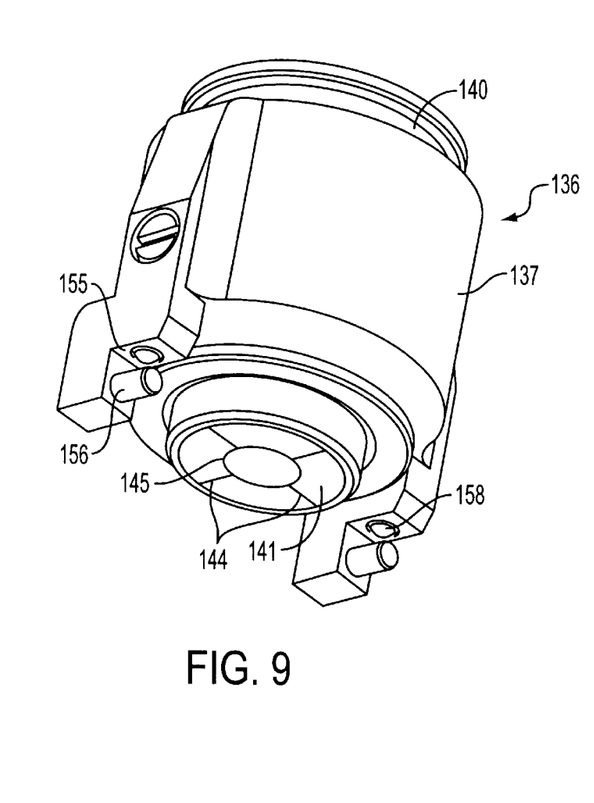
FIGS. 9 and 10 show a tonometer in a dismounted and mounted position, FIGS. 11 and 12 schematically illustrate a control unit.

FIG. 9 and 10 show a tonometer 136 for use with the microkeratome of the present invention. The tonometer 136 comprises a housing 137 of titanium with a cylindrical boring 138 which, in the mounted position shown in FIG. 10, is coaxial to the axis 29. On the upper and lower end of the boring 138, two low-friction thermoplastic slide rings 139 are inserted in corresponding grooves. Two cylindrical sleeves 140 are slideably guided by the rings 139. The sleeves 140 are pressed or bonded onto a cylindrical, transparent sapphire body 141 which has a plane lower end surface 142 perpendicular to the axis 29 and a spherical upper surface 143. The lower surface 142 has engraved or etched cross lines 144 of which one, in the mounted position, is parallel to the guide rails 27 and the other one is perpendicular to it. The lines 144 cross the axis 29. The lower surface further has a circular mark 145. A pin 146 screwed into the housing 137 engages a longitudinal groove 147 in one of the sleeves 140 and guarantees an accurate angular position of the cross lines 144.

The upper face of the suction ring 11 has two diametrically opposed upstanding bosses 151 (not shown in FIG. 1 to 6) with plane upper surfaces 152 which contain spherical or cylindrical recesses 153. Each boss 151 further comprises a boring 154 parallel to the rails 27. The housing 137 has corresponding contract surfaces 155 for contacting the surfaces 152 and pins 156 for insertion into the borings 154. The housing 137 further has two inserts 157 with spring loaded balls 158 which snap into the recesses 153 when the tonometer 136 is mounted on the suction ring 11.

Figure 11:
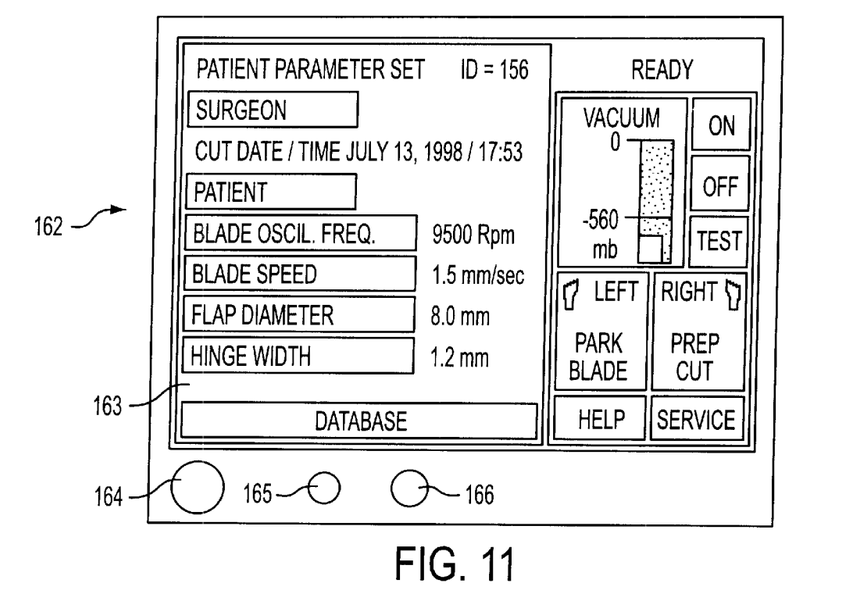
Figure 12:
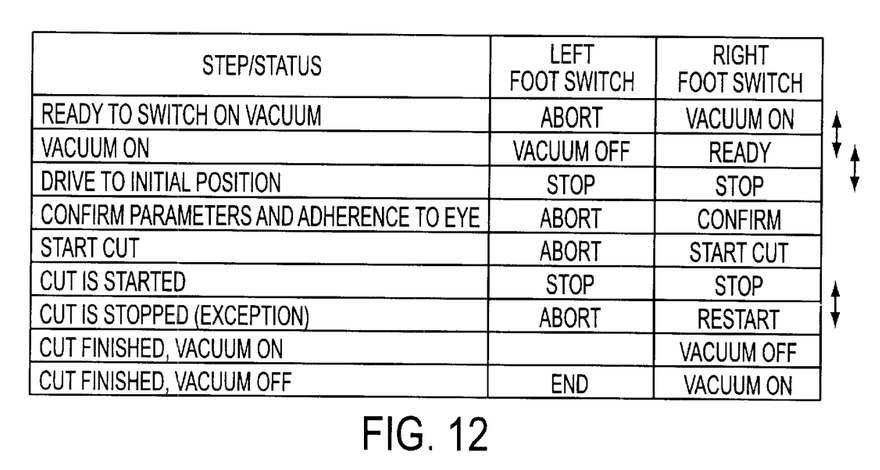

The microkeratome further comprises a control unit 162 (FIG. 11) with a touch screen 163, a socket 164 for plugging in a plug at the end of the cable 105, a connector 165 for connecting the unit 162 with the connector 23 by a vacuum house (not shown), and a socket 166 for plugging in a cable to two foot switches (not shown). The control unit 162 contains a vacuum pump, a vacuum vessel, a vacuum switch, a vacuum sensor and a programmable microprocessor.

Before starting an operation, the motor unit 6 with cover 90 and connection holder 101 are suspended on the rails 92 in a stand. These units need not to be sterilized because they do not come into contact with the patient or with the surgeon's hands. They may, however, be sterilized with gas. The holder 1 with grip unit 9, the slide 2 and the tonometer 136 are sterilized in an autoclave. The sled 3 with blade 4, mounting help 7 and handle 8 are contained in a sterile sachet or box. The patient's eye 13 is marked by a conventional stamp known as LASIK-marker with cross lines crossing the axis of the eye and with a small circle around that axis. The surgeon enters his name to the control unit 162, whereupon his last used set of parameters appears on the touch screen. He enters the patient's name and changes the parameters if required. When he touches one of the fields with parameter denomination, a new keyboard appears which allows the corresponding entry. For the numerical parameters a numerical keyboard is displayed and for names an alphanumerical one. The cables and the hose are connected to the control unit 162.

For the assembly of the microkeratome, first the sled 3 is inserted into the slide 2 up to abutment of the step 58 of the handle 8 on the slide 2. In this position the slot 59 is centered in the axis of the opening 77. The slide 2 is then pushed onto the extension 71. The bars 70 automatically snap into the grooves 72. The pin 89 enters the conical recess 60 and automatically centers the slot 59 to the pin 89. The mounting help 7 and the handle 8 are removed. Now the holder 1 is inserted with its rails 27 into the grooves 30 of the slide 2 from behind. The shoe 87 enters the groove 34 which is best seen in FIG. 13 which shows a cross section along the upper surface 32 of the raised part 31 of the holder 1. The axis 169 of the disc 85 and the output shaft 84 of the motor 82 is marked with a circle. This axis 169 is parallel to the middle plain 28 but offset to one side. The rotary position of the shoe 87 with respect to the axis 169 is shown in solid lines in FIG. 13. The holder 1 is pushed forward until the shoe 87 abuts the rear face 170 of the groove 33.

Now the pusher 110 is pushed in so that the holder 101 is decoupled from the motor unit 6 and coupled to the gripping unit 9. The signal of the sensor 130 initiates a rotation of the output shaft 84 by about 10° so that the shoe 87 enters the groove 33 and reaches the position shown in dashed lines in FIG. 13. The slide 2 is now in its parking position shown in FIG. 3 and 4. The microkeratome still hangs with its rails 92 in its stand and is ready to start operation.

The tonometer 136 may now be attached to the suction ring 11 and the surgeon grips the microkeratome and places the suction ring 11 on the patient's eye 13 such that the cross lines 144 are exactly aligned with the cross lines marked on the patient's eye. The vacuum is now switched on with the right foot switch so that the suction ring adheres to the eye 13 and is immobilized relative to the eye. The eye pressure is checked. The gravitational force of the body 141 and sleeves 140 creates a certain, visible contact area which should not be larger than the area marked with the circle 145.

If this is the case, the tonometer 136 is removed and the slide 2 is moved to its initial position by pressing the right foot switch. The shoe 87 -it then in the position shown in dashed lines in FIG. 13 and the plate 39 has moved forward so that the end face 41 is somewhat ahead of the axis 29. The cutting edge 5 is a specified distance h away from the axis 29, e.g. 6 mm.

Some surgeons have so much experience that they do not need a tonometer but feel the eye pressure with a finger. In that case, cross lines 170 on the suction ring are used for centering the suction ring on the eye 13. The plate 39 is transparent and has a set of marks 171 with increasing radius on its top or bottom surface around the axis 29 in the initial position of the slide 2. The surgeon reads the diameter of the contact surface of the plate 39 with the eye 13 with the help of these marks 171 and enters the value on the touch screen 163. He checks whether all parameters are correct and confirms them by pressing the right foot switch. By pressing, that switch again, the cut is started and the microkeratome now operates the way described in U.S. patent application Ser. No. 09/129,365 mentioned above. The control unit 163 varies the angular speed of the disc 85 such that the linear speed of the slide 2 is constant and corresponds to the set value. The total angle of rotation is calculated from the distance h, the flap diameter and the hinge width.

After the cut is finished, the slide 2 returns to the park position and the vacuum is switched off with the right foot switch. Disassembly of the microkeratome for cleaning and sterilizing is done in the reverse order of the assembly. The sled 3 and blade 4 are disposed.

A test program may be run prior to use by touching the screen 163 on the field "test". An insert is then shown on the touch screen instead of the fields "database", "help" and "service" and the program, which checks the various functions and the vacuum by pinching at a certain stage the vacuum tube is run through with the foot switches. This test only takes a few seconds.

The overwhelming majority of surgeons use steel blades 4 in microkeratomes. These blades are rather expensive since they are used only a single time. Another possibility is the use of diamond blades which are cheaper in the long run and have a number of advantages, in particular a much sharper cutting edge which results in a cleaner cut. The rpm of the motor 83 can be set lower or it may not even be necessary to vibrate the blade 4, thus reducing vibrations. A diamond blade can be used indefinitely if properly handled.

However, the cutting edge of a diamond blade is extremely vulnerable. The blade must be disassembled from the side after use for claiming and sterilizing.

Figure 14:
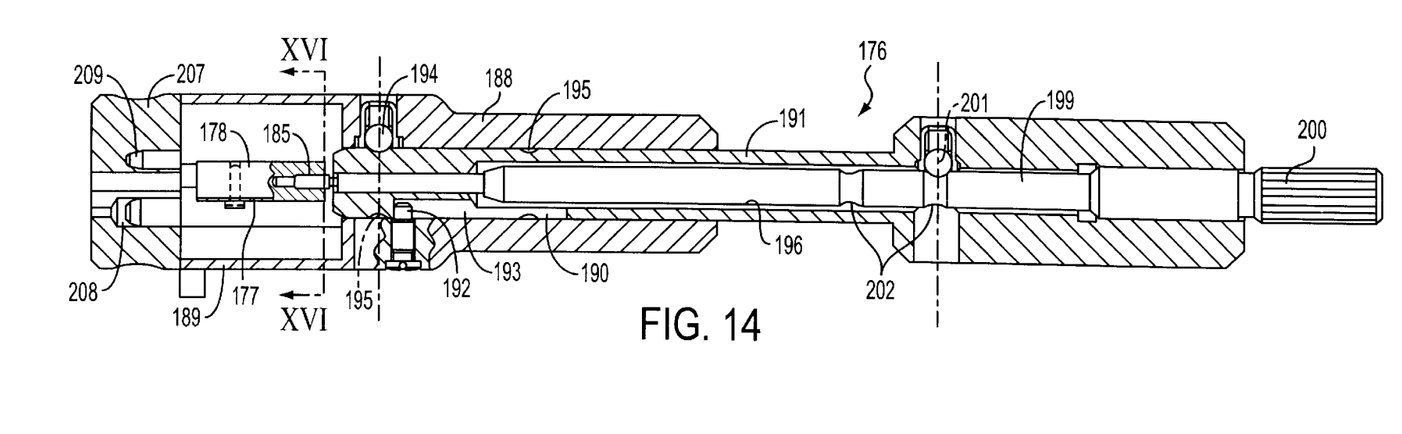
FIGS. 14 to 16 show a mounting unit for a diamond blade.
Figure 15:
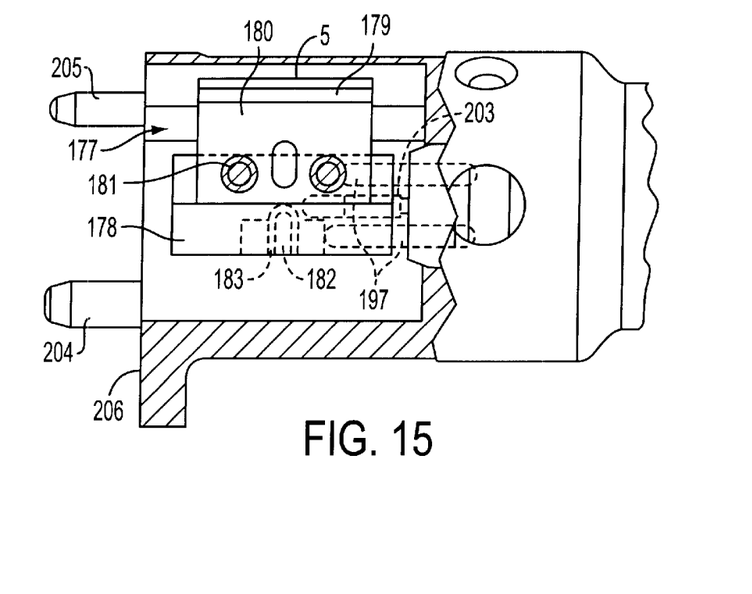
Figure 16:
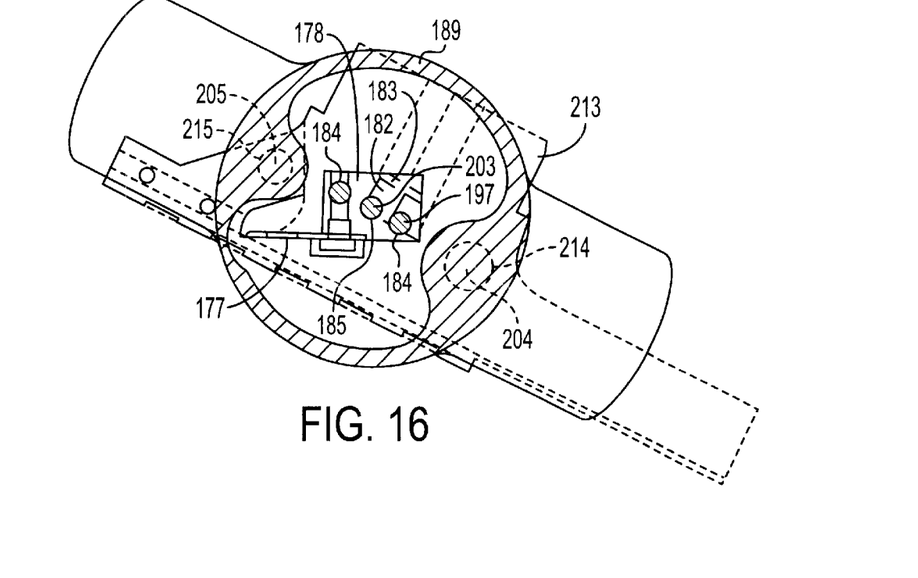

FIG. 14 to 16 show a holder and mounting unit 176 for such a diamond blade. The blade 177 and sled 178 are actually designed for the microkeratome according to U.S. patent application Ser. No. 09/129,365 (without the elastic arm 46 of the sled 31 and therefore with a different shape of the opening 44) but it is intended to later use a sled comparable to the one show in FIG. 7 and 8. The elastic arm 46 would in this case have to include a cylindrical body to accommodate the female thread, and the extension 57 may need a snap action fit to the arm 46 (FIG. 7 and 8).

The blade 177 consists of a narrow diamond blade 179 vacuum-hard-braced onto a steel blade 180 of the same thickness. The blade 180 is screwed onto the prismatic sled 178 by screws 181. The slot 182 and the wedge-shaped countersink 183 correspond to the slot 59 and countersink 60 of FIG. 8. On one of its face surfaces the sled 178 has two borings 184 and in the center a female thread 185.

The unit 176 has a sleeve-shaped holder 188 with a cup-shaped end 189 and a thoroughgoing boring 190. A shaft 191 is slideable in the boring 190 and fixed against rotation by a pin 192 engaged in a longitudinal groove 193. A spring loaded ball 194 engages in one of two axially spaced circumferential grooves 195 of the shaft 191 to fix its two longitudinal positions. The shaft 191 has a thoroughgoing stepped longitudinal boring 196, and on its forward end two pins 197 engaging the borings 184.

A pin 199 with a gripping end 200 is slideable and rotatable in the boring 196. The axial position of the pin 199 is held by a spring urged ball 201 engaging one of two grooves 202. The forward end of the pin 199 has a male thread 203 matching the thread 185. Two pins 204, 205 of different diameters project from the plane end face 206 parallel to the axis of the pin 199. These pins match with corresponding borings of the slide. Before use a cover with corresponding borings 208, 209 is slid onto these pins 204, 205.

After use of the microkeratome the unit 176 is docked to the slide of the microkeratome by the two pins 204, 205. The pin 199 is pulled back and the shaft 191 moved to its forward position. The pin 199 is then moved forward and rotated so that the screw 203 screws into the thread 185. The motor unit is now removed from the slide and the shaft 191 pulled back. The sled 178 with the blade 177 is cleaned e.g. in an ultrasound bath and sterilized, and the end 189 is covered by the cover 207. For mounting the sled 178 the unit 176 is again docked to the slide of the microkeratome and the shaft 191 and pin 199 moved to their forward position. In this position the slot 182 is centered in the middle of the slide so that the motor unit can be mounted as described above.

The dashed lines in FIG. 16 indicate the slide 213 corresponding to the slide 30 of U.S. patent application Ser. No. 09/129,365 but adapted for docking of the unit 176. To that end one side of the slide 213 has two borings 214, 215 for receiving the pins 204, 205 and aligning mounting unit 176 on slide 213. The sled 178 has on its end surface a female thread 185 and borings 184 for coupling sled 178 to mounting unit 176, With this mounting unit 176 it is ensured that the blade 177, and in particular the diamond blade 179, is handled extremely carefully when mounting and dismounting the sled 178 and when cleaning it. There is no risk of touching the cutting edge 5 with an object or with a finger.

What is claimed is:

1. A cutting instrument, comprising:
   a holder with a linear first guide element extending in a first direction,
   a slide with a second guide element engaging the first guide element, the slide being displaceable in the holder in the first direction,
   the slide further comprising a first guide surface extending in a first plane and a second guide surface extending in a second plane which intersects the first plane along an intersecting line which is transverse to the first direction,
   a sled movably mounted on the slide for oscillating movement in a second direction which is parallel to the intersecting line,
   an elastic arm rigidly mounted on the sled and having a free end,
   a cutting blade mounted on the free end of the arm, the cutting blade having a cutting edge which is parallel to the second direction, the arm elastically biasing the blade against the first guide surface and against the second guide surface, and
   motor means for moving the slide on the holder in the first direction and for oscillating the sled in the second direction.

2. A cutting instrument comprising:
   a slide with a throughgoing transverse opening in a longitudinal direction, the opening having a non-circular first cross-section, and a slot extending from the opening;
   a sled slidably and removably inserted in the opening, the sled having a second cross-section which conforms to at least part of the first cross-section, the sled having a first and a second end surfaces, the end surfaces being substantially perpendicular to the longitudinal direction;
   a cutting blade with a cutting edge attached to the sled in a mounted position the blade extending through the slot; and
   a mounting-unit comprising a guide element and a handle, the guide element being detachably mounted to the first end surface of the sled, a cross-section of the guide element corresponding to a part of the first cross-section, the holder being detachably mounted on the second end surface of the sled.

3. The instrument of claim 2 wherein the holder has abutment means for abutment against a surface of the slide for centering the sled in the slide.

4. A cutting instrument comprising:
a slide with a throughgoing transverse opening in a longitudinal direction, the opening having a non-circular first cross-section, and a slot extending from the opening;
a sled slidably and removably inserted in the opening, the sled having a second cross-section which conforms to at least part of the first cross-section, the sled having an end surface, the end surface being substantially perpendicular to the longitudinal direction;
a diamond cutting blade with a cutting edge attached to the sled in a mounted position the blade extending through the slot;
the sled on its end surface-having a first coupling means, a face of the slide facing the same side as said end surface having a first alignment means;
the cutting instrument further comprising a mounting unit for mounting and dismounting the sled with the blade, the mounting unit comprising a holder and a coupling unit axially movable in the holder, the coupling unit on one end having second coupling means for connection to the first coupling means, the holder comprising second alignment means cooperating with the first alignment means to align the holder on the slide.

5. A cutting instrument comprising:
a holder with a linear first guide element extending in a first direction, the first guide element being open towards a front end of the holder;
a slide with a second guide element engaging the first guide element and being open towards a rear side of the holder such that the slide is removably inserted in the holder and movable in the first direction;
a motor mounted on the slide;
wherein the motor has a drive connection to an arm rotatable about an axis substantially perpendicular to the first direction, the arm carrying an eccentric pin with a shoe which engages in a lateral groove of the holder extending in a second direction which is substantially perpendicular to the first direction and to the axis, the lateral groove on one end merging into a longitudinal groove which is open in a direction towards the front end of the holder.

6. An instrument comprising:
a holder;
a slide movably mounted on the holder;
a motor unit removably mounted on the slide for affecting movement of the slide relative to the holder; wherein a cable to the motor unit is mounted to a cable holder, which has a flexible cable connection to the motor unit and is mechanically coupled to the motor unit when the motor unit is detached and is mechanically discoupled from the motor unit and coupled to the holder when the motor unit is mounted, a switching device switching the coupling connection between those two states.

7. A cutting instrument comprising a sled, a cutting blade having a cutting edge, an elastic arm integrally formed on the sled with attachment pins, the blade having holes which match the pins, the cutting instrument further comprising a mounting help to facilitate introduction of the sled and the cutting blade into an opening of a slide and a handle with a step spaced apart from the sled; the mounting help and the handle each formlockingly engaging the sled.

8. The cutting instrument of claim 7, wherein the pins of the blade have free ends and wherein the blade is attached to the sled by thermoplastic deformation of said free ends.

9. The cutting instrument of claim 7, wherein the sled, the handle and the mounting help each has a prismatic shape.

10. The cutting instrument of claim 7, wherein the sled is made of a thermoplastic material.

* * * * *